United States Patent
Doherty et al.

(10) Patent No.: US 9,883,852 B2
(45) Date of Patent: Feb. 6, 2018

(54) ULTRASOUND SYSTEMS, METHODS AND COMPUTER PROGRAM PRODUCTS FOR ESTIMATING TISSUE DEFORMATION WITH HARMONIC SIGNALS

(71) Applicant: Duke University, Durham, NC (US)

(72) Inventors: Joshua Doherty, Durham, NC (US); Jeremy J. Dahl, Durham, NC (US); Kathryn R. Nightingale, Durham, NC (US); Gregg E. Trahey, Durham, NC (US)

(73) Assignee: Duke University, Durham, NC (US)

( * ) Notice: Subject to any disclaimer, the term of this patent is extended or adjusted under 35 U.S.C. 154(b) by 476 days.

(21) Appl. No.: 14/216,275

(22) Filed: Mar. 17, 2014

(65) Prior Publication Data

US 2014/0276049 A1  Sep. 18, 2014

Related U.S. Application Data

(60) Provisional application No. 61/852,084, filed on Mar. 18, 2013.

(51) Int. Cl.
*A61B 8/00* (2006.01)
*A61B 8/08* (2006.01)

(52) U.S. Cl.
CPC ............ *A61B 8/5223* (2013.01); *A61B 8/485* (2013.01); *A61B 8/54* (2013.01); *A61B 8/461* (2013.01); *A61B 8/469* (2013.01)

(58) Field of Classification Search
None
See application file for complete search history.

(56) References Cited

U.S. PATENT DOCUMENTS

| | | | |
|---|---|---|---|
| 6,514,205 B1* | 2/2003 | Lee | G01S 7/52026 367/138 |
| 2004/0230121 A1* | 11/2004 | Hansen | A61B 8/481 600/458 |
| 2005/0277835 A1* | 12/2005 | Angelsen | A61B 8/14 600/437 |
| 2006/0052699 A1* | 3/2006 | Angelsen | G01S 15/8952 600/437 |
| 2009/0005682 A1* | 1/2009 | Fan | A61B 8/485 600/443 |

(Continued)

OTHER PUBLICATIONS

Doherty, et al. "A harmonic tracking method for acoustic radiation force impulse (ARFI) imaging", 2012 IEEE International Ultrasonics Symposium Proceedings, pp. 208-211.*

(Continued)

*Primary Examiner* — Katherine Fernandez
*Assistant Examiner* — Bradley Impink
(74) *Attorney, Agent, or Firm* — Myers Bigel, P.A.

(57) ABSTRACT

An ultrasound system for estimating tissue deformation in ultrasound elasticity imaging includes a controller configured to deliver a plurality of tracking pulses and to obtain a plurality of data sets for a region of interest from an ultrasound transducer array; a harmonic data analyzing circuit configured to receive the plurality of data sets and to extract one or more harmonic data sets including harmonic signals from the plurality of image data sets; and a displacement estimator circuit configured to estimate tissue deformation in the region of interest responsive to the one or more harmonic data sets.

8 Claims, 7 Drawing Sheets

(56) References Cited

U.S. PATENT DOCUMENTS

| | | | | |
|---|---|---|---|---|
| 2009/0048516 A1* | 2/2009 | Yoshikawa | ............... | A61B 8/08 600/443 |
| 2009/0178483 A1* | 7/2009 | Angelsen | ................. | A61B 8/08 73/597 |
| 2012/0232388 A1* | 9/2012 | Curra | ..................... | A61B 8/466 600/438 |
| 2013/0237820 A1* | 9/2013 | Vappou | .................. | A61B 8/485 600/438 |

OTHER PUBLICATIONS

Ma et al., Improvement of tissue harmonic imaging using the pulse inversion technique, Ultrasound in Med & Biol., vol. 31, No. 7, pp. 889-894, 2005.*

* cited by examiner

ULTRASOUND SYSTEMS, METHODS AND COMPUTER PROGRAM PRODUCTS FOR ESTIMATING TISSUE DEFORMATION WITH HARMONIC SIGNALS

RELATED APPLICATIONS

This application claims priority to U.S. Provisional Application Ser. No. 61/852,084 filed Mar. 18, 2013, the disclosure of which is hereby incorporated by reference in its entirety.

FIELD OF THE INVENTION

The present invention relates to ultrasound systems, methods and computer program products for estimating tissue deformation.

BACKGROUND

Ultrasound-based elasticity imaging methods rely upon accurate estimates of tissue deformation to characterize the mechanical properties of soft tissues. These methods may be corrupted by clutter, which can bias and/or increase variance in displacement estimates. There remains a need to reduce clutter and to improve axial resolution in ultrasound elasticity images.

SUMMARY

According to some embodiments, an ultrasound system for estimating tissue deformation in ultrasound elasticity imaging includes a controller configured to deliver a plurality of tracking pulses and to obtain a plurality of data sets for a region of interest from an ultrasound transducer array; a harmonic data analyzing circuit configured to receive the plurality of data sets and to extract one or more harmonic data sets including harmonic signals from the plurality of image data sets; and a displacement estimator circuit configured to estimate tissue deformation in the region of interest responsive to the one or more harmonic data sets.

In some embodiments, the plurality of tracking pulses include two or more tracking waveforms and the plurality of data sets comprise echo signals corresponding to the two or more tracking waveforms. The harmonic data analyzing circuit is configured to extract one or more harmonic data sets by combining the echo signals, and the two or more tracking waveforms differ in at least one transmit parameter such that, when the echo signals corresponding to the two or more waveforms are combined by the harmonic data analyzing circuit, at least one of a fundamental and a harmonic signal portion is increased and or decreased. The at least one transmit parameter may include a transmit waveform phase and/or amplitude.

The two or more tracking pulses may include two or more phase-inverted waveforms transmitted alternately in a common tracking location. The harmonic data analyzing circuit may be configured to combine the echo signals from the two or more phase-inverted waveforms to thereby reduce or substantially cancel a fundamental portion of the echo signals and to increase an amplitude of a harmonic portion of the echo signals. The two or more phase-inverted waveforms may include at least three or more phase-inverted waveforms, and the harmonic data analyzing circuit may be configured to extract the one or more harmonic data sets by combining the echo signals from at least first and second ones of the phase-inverted signals to increase an amplitude of a harmonic portion of the echo signals to provide a harmonic signal for the one or more harmonic data sets, and by combining the echo signals from at least second and third ones of the phase-inverted signals to increase an amplitude of at least some of a harmonic portion of the echo signals to provide another harmonic signal for the one or more harmonic data sets. A temporal sampling rate of the harmonic data sets may be substantially the same as a temporal sampling rate of the plurality of tracking pulses.

In some embodiments, the two or more tracking waveforms include at least three or more tracking waveforms, and the harmonic data analyzing circuit is configured to extract the one or more harmonic data sets by combining the echo signals from at least first and second ones of the tracking waveforms to increase and/or decrease an amplitude of at least one of a harmonic portion and a fundamental portion of the echo signals to provide a harmonic signal for the one or more harmonic data sets, and combining the echo signals from at least second and third ones of the tracking waveforms to increase and/or decrease an amplitude of at least one of a harmonic portion and a fundamental portion of the echo signals to provide another harmonic signal for the one or more harmonic data sets.

In some embodiments, the harmonic data analyzing circuit is configured to extract one or more harmonic data sets by applying a bandpass generally centered at a predetermined harmonic frequency. The filter may be a bandpass filter, a finite impulse response (FIR) filter, and/or a digital infinite impulse response (IIR) filter.

In some embodiments, the controller is configured to emit an acoustic radiation force excitation to the region of interest with an ultrasound transducer array.

In some embodiments, the controller is configured to apply a compression and/or vibration to the region of interest by strain imaging, elastography and/or sonoelasticity.

In some embodiments, a tissue deformation is estimated by a phase-shift and/or correlation-based estimation.

In some embodiments, a tissue deformation is estimated by the deformation estimation circuit by calculating a maximum displacement time, a displacement value at a predetermined time, a time to percent recovery of a maximum displacement, a mean displacement tissue and/or blood velocities and/or cross-correlation values and/or a parameter derived from a displacement response.

In some embodiments, the controller is configured to display an image of the region of interest responsive to the estimate of tissue deformation on a display.

According to some embodiments, an ultrasound method for estimating tissue deformation in ultrasound elasticity imaging includes delivering a plurality of tracking pulses and to obtain a plurality of data sets for a region of interest from an ultrasound transducer array; extracting one or more harmonic data sets comprising harmonic signals from the plurality of image data sets; and estimating tissue deformation in the region of interest responsive to the one or more harmonic data sets.

According to some embodiments, a computer program product for estimating tissue deformation in ultrasound elasticity imaging is provided. The computer program product includes a computer readable medium having computer readable program code embodied therein. The computer readable program code includes computer readable program code configured to deliver a plurality of tracking pulses and to obtain a plurality of data sets for a region of interest from an ultrasound transducer array; computer readable program code configured to extract one or more harmonic data sets comprising harmonic signals from the plurality of image data sets; and computer readable program code configured to estimate tissue deformation in the region of interest responsive to the one or more harmonic data sets.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 8a was obtained from the same subject as FIGS. 5a-5d, FIG. 8b was obtained from the same subject as FIGS. 6a-6b, and FIG. 8c was obtained from the same subject as FIGS. 7a-7b.

DETAILED DESCRIPTION

Figure 1A:
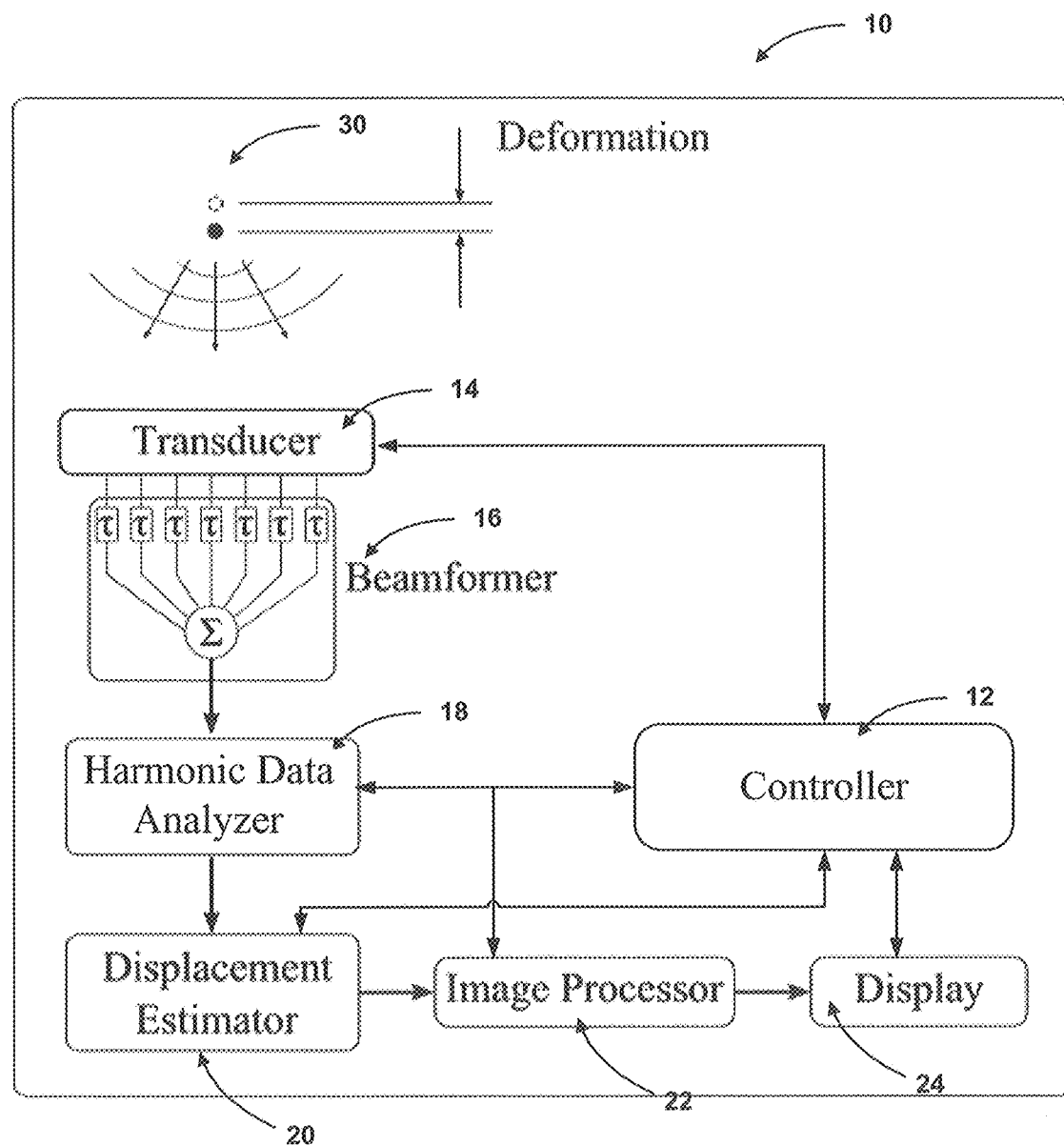
FIG. 1a is a schematic diagram of an ultrasound system according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

With reference to FIG. 1a, an ultrasound system 10 according to some embodiments is shown. The ultrasound system includes a controller 12 that is in communication with an ultrasound transducer array 14 with a beamformer 16, a harmonic data analyzer 18, a displacement estimator 20, an image processor 22 and a display 24. As shown in FIG. 1a, the ultrasound transducer array 14 is configured to transmit and receive ultrasound signals from a region of interest 30. It should be understood that the components of the ultrasound system 10 described herein may include hardware, such as circuits and computer processors, as well as tangible computer readable media for storing computer readable program code to perform the operations described herein.

Figure 1B:
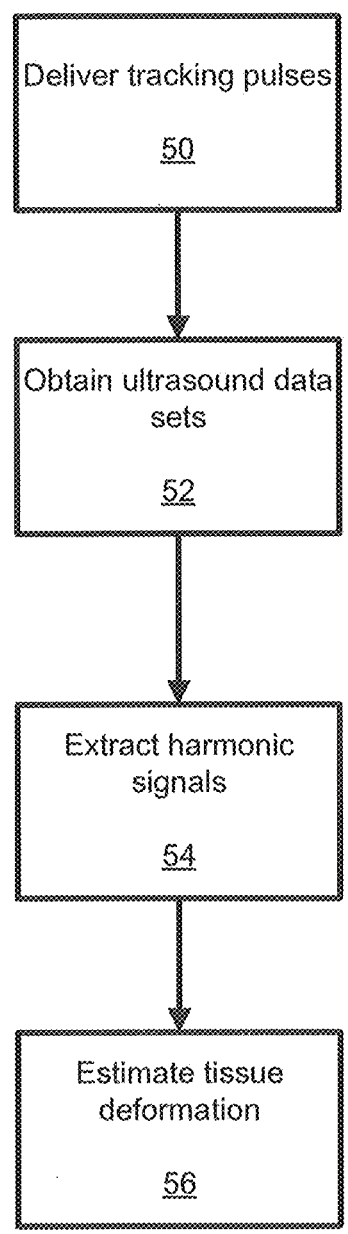
FIG. 1b is a flowchart of operations according to some embodiments.

With reference to FIGS. 1a-1b, the controller 12 is configured to deliver a plurality of tracking pulses and to obtain data sets for the region of interest 30 with the ultrasound transducer array 14 (FIG. 1b, Blocks 50 and 52). The harmonic data analyzer 18 is configured to receive the data sets, to extract one or more harmonic data sets including harmonic signals from the image data sets (FIG. 1b, Block 54). The displacement estimator 20 is configured to estimate tissue deformation in the region of interest 30 responsive to the harmonic data sets (FIG. 1b, Block 56).

In some embodiments, the tracking pulses include the two or more tracking waveforms that differ in at least one parameter. The parameter may be selected so that, when corresponding echo signals of the tracking waveforms are combined, a fundamental portion and/or a harmonic portion of the echo signal is increased or decreased. Accordingly, the tracking waveforms may be selected so that various harmonic and/or fundamental portions of the corresponding echo signals may be increased or decreased (or substantially canceled). The parameter may be an amplitude and/or phase difference in successive tracking waveforms. In particular embodiments, the tracking pulses include two or more phase-inverted waveforms transmitted alternately in a common tracking location. As illustrated in FIG. 1, the tissue in the region of interest experiences a displacement or deformation. Ultrasound-based elasticity imaging techniques may be used to characterize the mechanical properties of soft-tissues based on measured deformations. The source of excitation used to elicit the deformation can vary. For instance, an impulsive (i.e., short-duration) acoustic radiation force excitation may be applied using a focused ultrasonic transducer. Examples of acoustic radiation force excitation are described in U.S. Pat. No. 6,371,912 to Nightingale, the disclosure of which is hereby incorporated in its entirety. An acoustic radiation force excitation is a "pushing" pulse that has sufficient energy to cause physical displacement of the tissue. However, other techniques for displacing or deforming the tissue may be used, including other excitation sources such as physiological based sources (i.e., cardiac motion) and externally applied compression or vibration as performed in methods including strain imaging, elastography, and sonoelasticity. Regardless of the excitation source, the ultrasonic transducer array 14 is used to receive echoes from the region-of-interest (ROI). As depicted in FIG. 1, the received echoes are beamformed by the beamformer 16 to create a focused radiofrequency (RF) signal. To monitor the deformation response, multiple RF signals may be recorded at the pulse-repetition frequency (PRF) both before (reference signals) and after (tracking signals) the excitation is applied.

From the beamformed RF signals, the harmonic components can be obtained with the harmonic data analyzer 18. Example techniques for extracting the harmonic components of the signals include, but are not limited to 1) a filter-based approach and 2) a phase-inverted (PI) method. With the filter-based approach, the harmonic components can be obtained by using a bandpass filter centered at the desired harmonic frequency. With the PI method, phase-inverted (+ and −) waveforms may be transmitted alternately in a single tracking location and then received by the transducer. The combining of two phase-inverted signals, for example, by summing or subtracting the signals, will substantially cancel the fundamental and odd harmonics while doubling the even harmonics.

Figure 2:
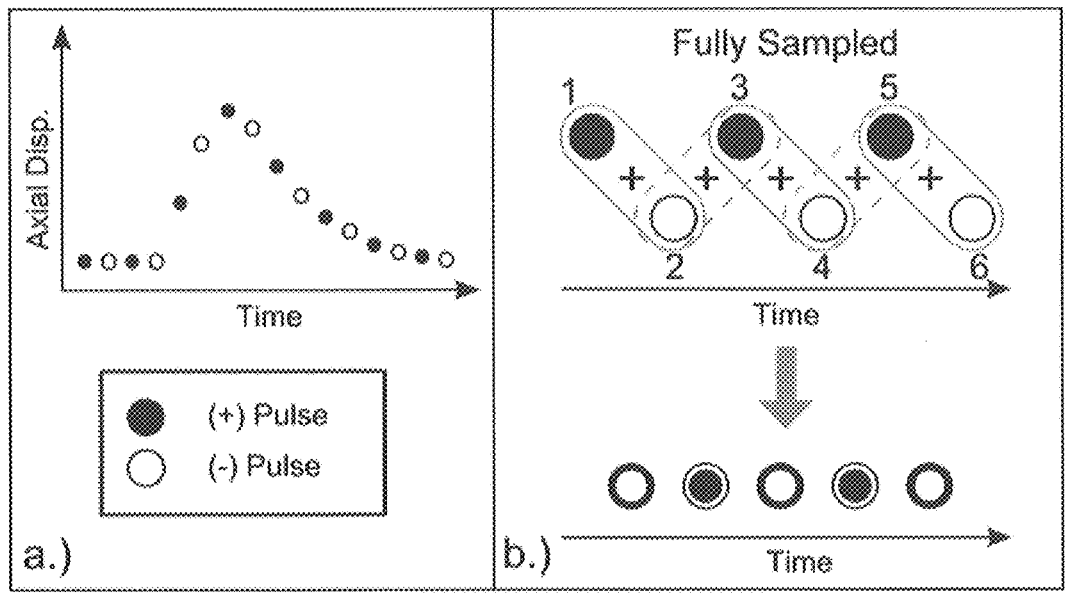
FIG. 2a is a graph of an Acoustic Radiation Force Impulse (ARFI) deformation response that is monitored using a pulse-inversion scheme that transmits pulses of alternating polarity for a period that begins before the excitation and extends for a duration beyond the peak displacement response according to some embodiments.
FIG. 2b is a schematic diagram of a fully sampled pulse-inversion technique in which each positive polarity pulse is summed with the subsequent negative polarity pulse, and each negative polarity pulse is also summed with the subsequent positive polarity pulse.

In some embodiments, a fully-sampled scheme with a temporal sampling rate substantially equal to the PRF of the transmitted waveforms may be provided. FIG. 2a is a typical deformation response curve portraying the axial displacements before and after the application of an impulsive acoustic radiation force excitation that are alternately tracked through time with the phase-inverted signals. The proposed fully sampled PI method in FIG. 2b sums the phase-inverted signals to create a harmonic signal without a reduced frame rate. In addition, the proposed invention also includes the use of interpolation schemes to reduce motion artifacts on the phase-inverted signals prior to combining. As shown in FIG. 2b, the first and second phase-inverted signals are summed, and the second and third phase-inverted signals are summed. In other words, each signal is summed with both a preceding phase-inverted signal and a subsequent phase-inverted signal. In contrast, conventional B-mode phase-inverted techniques typically only sum pairs of phase-inverted signals once, i.e., the first and second phase-inverted signals are summed and the third and fourth phase-inverted signals would be summed without combining the second and third signals. By combining each signal with both a preceding and a subsequent signal, the temporal sampling rate may be increased so that it is substantially equal to the PRF of the transmitted waveforms.

An estimate of the soft-tissue deformation between two received signals can be calculated from the harmonic data by the displacement estimator 20. The estimate of deformation may be calculated with, but is not limited to, phase-shift or correlation-based estimators that are currently employed in ultrasound Doppler and elasticity imaging methods. In the image processor 22, these displacement estimates and cross-correlation values may be used to calculate quantitative and/or qualitative measures which are then output to the display 24. This may include, but is not limited to, calculating the maximum displacement occurring through time, the displacement at a particular time, time to percent recovery of the maximum displacement, tissue and/or blood velocities, and cross-correlation values.

In some embodiments, the bias and jitter in displacement estimates introduced by the presence of clutter may be reduced for improved imaging contrast. For example, in Acoustic Radiation Force Impulse (ARFI) imaging, large amounts of clutter due to near-field reverberation can make it difficult to track the induced deformations in abdominal structures such as the liver. In order to differentiate structures such as tumors from healthy tissues, existing methods require higher acoustic intensities in order to achieve deformations that are large enough to be tracked in the presence of increased jitter. With decreased jitter, due to clutter suppression, the harmonic tracking methods described herein may allow for the ability to measure smaller deformations and thereby require decreased acoustic pressures and improved sensitivity. For ARFI, where the deformation and recovery of soft-tissues is a transient response (i.e., typically <2 msec.), the fully sampled PI techniques described in FIG. 2a-2b also may improve the ability to estimate the maximum tissue displacement. The PI techniques described herein may also be sensitive to imaging blood flow where large motion that occurs between the phase-inverted signals typically results in poor canceling of the linear components when summed. For cardiovascular applications, this is useful for improved differentiation of tissue and blood components, where clutter due to reverberation within the artery and bright off-axis scatterers such as the arterial walls can make this differentiation difficult. Without a loss in frame rate, the fully sampled harmonic PI method improves the visualization of both 1) the arterial wall & lumen interface and 2) the interface of the arterial wall and surrounding tissues compared to conventional B-mode imaging.

With improved definition of the arterial wall, some embodiments may also include using harmonic ARFI imaging for measuring arterial thickness. Initial investigations have indicated an improved inter-reader consistency of arterial thickness measurements of harmonic ARFI imaging compared to intima-media thickness (IMT) measurements from B-mode images. Harmonic ARFI imaging may provide measurements of arterial thickness in more difficult to image patients and locations where standard B-mode IMT measurements cannot be made. In addition, the fully sampled PI approach may be useful in imaging slower blood flow and contrast/perfusion imaging. In this respect, clutter suppression associated with harmonic tracking may allow for improved visualization of small blood vessels/arteries or improved blood velocity estimates.

Embodiments according to the invention may be applicable for use on all forms of ultrasonic systems using any transducer technology. This includes, but is not limited to stand alone, portable, and/or handheld systems using phased, linear, curvilinear, intracardiac, intravascular, esophageal, and/or endocavity transducers using piezoelectric, single crystal, multi-layer composite, capacitive micro-machined ultrasonic transducers (CMUT), and/or hybrid technologies. The proposed techniques may also be combined with a variety of beamforming algorithms and processing methods including, but not limited to synthetic aperture methods, coherence based imaging, spatial and/or frequency compounding.

Although embodiments according to the present invention are described herein with respect to pulse-inversion tracking waveforms, it should be understood that any transmit parameter, including amplitude and/or phase parameters, may be used. The tracking waveforms may have differing amplitudes and/or phase parameters that are selected to provide corresponding pairs of echo signals that, when combined, increase, decrease and/or substantially cancel one or more portions of the individual echo signals, including a fundamental portion and/or harmonic portion of the individual echo signals. Therefore, the harmonic data analyzing circuit may combine pairs of echo signals as described herein that decrease and/or increase one or more of the harmonic portions of the signal or that decrease and/or increase the fundamental portion of the signal.

Embodiments according to the present invention will now be described with respect to the following non-limiting examples.

In some embodiments, pulses of opposite polarity are alternately transmitted at a pulse repetition frequency (PRF) equal to 1/tprf, where tprf is the pulse repetition time between subsequent transmits, to track the arbitrary displacement recovery curve in FIG. 2(a). In this idealized ARFI deformation response, the axial displacements are monitored for a period that begins before the excitation is applied and extends for a duration beyond the peak displacement response. By combining returned echoes with alternate pairs of pulse-inverted echoes, the fully sampled pulse-inversion method shown in FIG. 2(b) may be used to create a harmonic data set with a temporal sampling frequency equal to the PRF of the transmitted pulses.

Figure 3:
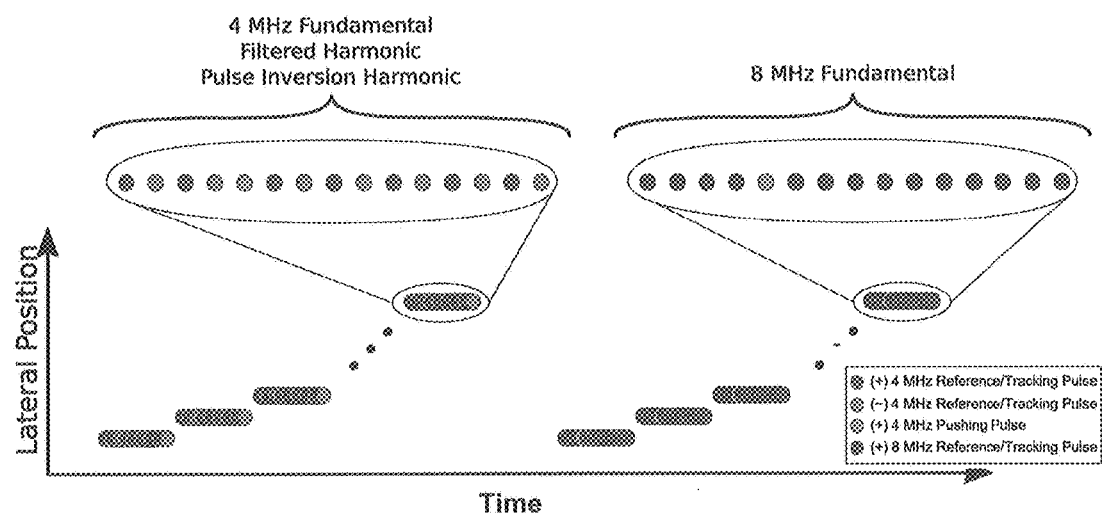
FIG. 3 is a schematic diagram of an ARFI pulse sequence according to some embodiments.

Custom pulse sequences were developed that acquire spatially-matched fundamental B-mode, fundamental ARFI, harmonic B-mode, and harmonic ARFI information within a single acquisition. As shown in FIG. 3, the ARFI pulse sequence consisted of two portions. In the first portion of the sequence, an ensemble of 4-MHz pulses that alternate in polarity was transmitted to monitor the deformation response at each of several spatially-distinct lateral locations. In the second portion of the sequence, an ensemble of 8-MHz fundamental pulses of identical polarity was transmitted at each of the same lateral locations that were used in the first portion of the sequence. As indicated, multiple images can be created from the echoes received using this pulse sequence, including: 1) 4-MHz fundamental, 2) filtered harmonic, and 3) pulse-inversion harmonic, all from the first portion of the sequence, and 4) 8-MHz fundamental data from the second portion of the sequence.

A 4-MHz 150-µs pushing pulse with an F/3 configuration was used in both portions of the sequence. The deformation response was monitored 0.7 ms before and 2.6 ms following the start of the acoustic radiation force excitation at a PRF of 9.4 kHz using a single on-axis (i.e., aligned with the center of the applied excitation) tracking beam. The excitation and tracking beam ensemble was applied at 50 distinct lateral locations uniformly distributed across a 15-mm FOV. The total duration of the pulse sequence was 420 ms. The pulse sequences were implemented on a diagnostic Acuson S2000 ultrasound scanner with a 9L4 linear-array transducer (Siemens Medical Solutions USA Inc., Issaquah, Wash.).

Data were acquired in calibrated, tissue-mimicking, elastic, homogeneous phantoms (CIRS Corp., Norfolk, Va.) with Young's Modulus (E) values of 4.5, 9, and 24 kPa, as determined by the manufacturer using an indenter system. In the phantoms, data were separately acquired at focal depths of 20 and 30 mm. Data were also acquired in vivo in the carotid artery of human subjects according to a protocol approved by the Institutional Review Board (Duke University Protocol ID: Pro00012795). All subjects provided written, informed consent before participation in the study. The study population included normal, healthy subjects with no known carotid artery plaques and subjects with carotid artery plaques that had been previously identified during a routine ultrasound exam. For each subject, three to five imaging data sets were acquired at multiple imaging locations, with a few seconds pause between acquisitions, to confirm spatial and temporal repeatability of the images.

In phantom and in vivo experiments, raw radio-frequency data were acquired at 40 MHz and processed off-line with Matlab (The MathWorks Inc., Natick, Mass.) software.

The pulse-inversion transmit scheme used in the first portion of the pulse sequence (FIG. 3) results in a halving of the temporal sampling frequency between returned echoes of identical polarity. To create the fully sampled 4-MHz fundamental data, the returned echoes of alternating polarity were separately tracked with respect to their own reference pulses, and then combined.

The harmonic components of the received radio-frequency data were obtained using both the filtered and pulse-inversion approaches. In the filtered approach, a 50-tap FIR band-pass filter centered at 8 MHz with a fractional bandwidth of 0.3 was applied to the fully sampled 4-MHz data to obtain the second-harmonic components. The pulse-inversion harmonic ARFI data was created using the fully sampled pulse-inversion harmonic method (FIG. 2(b)). Created from 4-MHz transmits, the 8-MHz (i.e., second-harmonic) components are most dominant in the pulse-inversion harmonic data.

The combining of two echoes separated in time, as performed in the fully sampled pulse-inversion harmonic approach (FIG. 2(b)), may function as a low-pass filter. To evaluate the impact of this potential averaging effect, 8-MHz fundamental radio-frequency data was summed according to the fully sampled pulse-inversion harmonic approach to create averaged 8-MHz fundamental data. Because the polarities of the summed 8-MHz fundamental echoes are identical, no fundamental cancellation occurs.

Axial displacement estimates were calculated using normalized cross-correlation (NCC) with a 1.5λ tracking kernel that was updated for the different frequencies between the fundamental and harmonic methods. In the homogeneous phantom experiments, outliers in the raw displacement estimates were removed by discarding estimates greater than the 95th percentile of the displacements measured at each depth and time following the start of the acoustic radiation force excitation. For in vivo data, quadratic motion filters were used to remove artifacts from non-ARFI-induced motion such as physiological and transducer motion. Unless otherwise stated, all ARFI images and corresponding displacement and normalized cross-correlation values represent estimates 0.80 ms after the start of the acoustic radiation force excitation. This specific time was chosen empirically because it was approximately the time at which maximum contrast was observed in all ARFI images.

The ARFI images and displacements reported herein correspond to the absolute magnitude of the estimated displacements. Previous studies have reported positive and negative high-magnitude displacement noise within the lumen of blood vessels in ARFI images. See B. J. Fahey, R. C. Nelson, D. P. Bradway, S. J. Hsu, D. M. Dumont, and G. E. Trahey, "In vivo visualization of abdominal malignancies with acoustic radiation force elastography," Phys. Med. Biol., vol. 53, pp. 279-293, 2008. Absolute magnitude images show improved visualization of the blood by reducing this spatially-variant noise within the lumen. Because negative displacements are not observed outside the lumen, depicting the absolute magnitude of the displacements does not affect the visualization of the soft tissue regions.

For each ARFI acquisition (i), the axial displacement ($\delta_{i,j,k}$) and associated normalized cross-correlation value ($\rho_{i,j,k}$) were estimated at each axial depth (j) and lateral location (k). In the homogeneous phantoms, the mean displacement ($\overline{\delta_{i,j}}$) and mean normalized cross-correlation value ($\overline{\rho_{i,j}}$), across all N=50 lateral locations, were determined according to $$\overline{\delta}_{i,j} = \frac{1}{N}\sum_{k=1}^{N}\delta_{i,k,j}$$

$$\overline{\rho}_{i,j} = \frac{1}{N}\sum_{k=1}^{N}\rho_{i,k,j}.$$

Because the true displacement is unknown, the mean displacement ($\overline{\delta_{i,j}}$) was used to estimate the jitter ($\psi_{i,j}$), the root-mean-square of the displacement error, for each phantom acquisition according to $$\psi_{i,j} = \sqrt{\frac{1}{N}\sum_{k=1}^{N}(\delta_{i,j,k}-\overline{\delta}_{i,j})^2}.$$

To compare the performance of the tracking methods in phantoms, we report the mean and standard deviation of the 1) mean displacement ($\overline{\delta}_{i,j}$), 2) jitter estimate ($\psi_{i,j}$), and 3) mean normalized cross-correlation coefficient ($\overline{\rho}_{i,j}$) value from ten independent acquisitions obtained at different spatial locations within the phantom for each tracking method.

Measurements of the mean and standard deviation of the measured axial displacements and normalized crosscorrelation values within the carotid artery wall of a normal, healthy subject are used to compare the tracking methods in vivo. In the presence of carotid artery plaques, which are known to be heterogeneous structures, variance in the displacement may actually correspond to different materials, such as lipid pools, intraplaque hemorrhage, and/or calcifications, within the arterial wall. For this reason, in the presence of carotid artery plaques, improvements will only be characterized on the basis of feature detection and qualitative improvements.

Contrast and contrast-to-noise ratio (CNR) were measured to quantify B-mode image quality according to $$\text{Contrast} = -20\log_{10}\left(\frac{S_i}{S_o}\right)$$

$$CNR = \frac{|S_i - S_o|}{\sqrt{\sigma_i^2 + \sigma_o^2}},$$

where Si and So represent the mean signal magnitudes inside and outside the region of interest, respectively, and $\sigma_i^2$ and $\sigma_o^2$ are the corresponding variances. For each image shown, the lumen and adjacent arterial walls were manually segmented to define the inside and outside regions, respectively. To preserve image clarity, the boundaries of these regions have not been identified in the images shown.

Results

Phantom Imaging: FIGS. 4a-4b compare the mean axial displacement, jitter estimate, and mean normalized cross-correlation among the fundamental and harmonic tracking methods in an E=9 kPa homogeneous, elastic, tissue-mimicking ultrasound phantom with a focal depth of 30 mm. The solid lines correspond to the mean value with shaded error bars representing one standard deviation across ten independent acquisitions. In some cases, especially for the mean displacement, the small magnitude of the error bars makes them difficult to visualize. In FIG. 4(a), the tracking methods are compared as a function of axial depth at a fixed time of 0.8 ins following the start of the acoustic radiation force excitation. Conversely, in FIG. 4(b), the methods are compared as a function of time following the start of the acoustic radiation force excitation at a fixed depth of 30 mm. The mean displacements are nearly identical for all tracking methods through depth (FIG. 4(a)) and time (FIG. 4(b)). Differences between the jitter estimates for the various tracking methods depend upon the specific time and depth, but are relatively small in magnitude for all cases. For most times and depths, the 4-MHz fundamental method has the largest normalized cross-correlation value, followed by the nearly identical 8-MHz fundamental and filtered harmonic methods, with the pulse-inversion harmonic method having the lowest normalized cross-correlation value. However, at the focal depth of 30 mm and at a time shortly following the peak displacement response, which is usually represented in an ARFI image, the normalized cross-correlation value of all methods is quite similar and in all cases is greater than 0.993. As a function of time following the start of the acoustic radiation force excitation, there is a subtle oscillation of the mean displacement, jitter estimate, and normalized cross-correlation values for the 4-MHz fundamental, filtered harmonic, and pulse-inversion harmonic data sets created from the pulse-inverted echoes (FIG. 4(b)). Similar small differences between the tracking methods demonstrated in this particular configuration were observed in phantoms of stiffnesses E=4.5 kPa and E=24 kPa and at focal depths of 20 and 30 mm.

In Vivo Imaging: FIGS. 5a-5d show matched B-mode and ARFI images of a carotid artery (CA) and jugular vein (IV) in a normal, healthy subject. Qualitatively, less clutter is observed within the lumen of the carotid artery in the harmonic B-mode images (FIGS. 5(c) and 5 (d)) compared with the fundamental B-mode images (FIGS. 5(a) and 5 (b)). This observation is consistent with contrast values of 21.42, 22.88, 25.03, and 28.61 db and CNR values of 0.97, 0.71, 1.01, and 0.95 that were measured in the 4-MHz fundamental, 8-MHz fundamental, filtered harmonic, and pulse-inversion harmonic B-mode images, respectively. In the jugular vein, a bright, coherent signal, indicated by the yellow arrows, is observed in the 4-MHz fundamental B-mode image (FIG. 5(a)). This apparent clutter signal is also observed in the 8-MHz fundamental B-mode image (FIG. 5(b)), but less so in the filtered harmonic B-mode image (FIG. 5(c)), and is barely noticeable in the pulse-inversion harmonic B-mode image (FIG. 5(d)). The narrow band-pass filter that was necessary to remove this artifact in the filtered harmonic B-mode image (FIG. 5(c)) appears to have degraded the axial resolution. Overall, there is a marked improvement in the delineation of the blood vessel interfaces along the proximal and distal walls, where they appear smoother in the harmonic B-mode images (FIGS. 5(c) and 5(d)). In particular, the boundary of the intima with the lumen in the distal wall is more clearly resolved in the pulse-inversion harmonic B-mode image (FIG. 5(d)).

In the ARFI images, because the applied acoustic radiation force magnitude is dependent upon focal and absorption effects, the key information portrayed is the relative displacement of a region of interest compared with that of surrounding tissues. In general, the stiff vessel walls have uniform displacement of low magnitude (i.e., less than 1 μm) compared with the softer, surrounding tissues with higher displacements. Relatively high magnitude displacement noise exists within the lumen of the ARFI images and is greatest in the harmonic ARFI images, particularly in the pulse-inversion harmonic ARFI image (FIG. 5(d)).

In the 4-MHz fundamental and 8-MHz fundamental ARFI images (FIGS. 5(a) and 5(b)), the proximal wall of the carotid artery is difficult to distinguish from surrounding tissues and the lumen of the jugular vein. A marked improvement in visualization of the proximal wall is demonstrated in the harmonic ARFI images, most notably with the pulse-inversion harmonic ARFI image (FIG. 5(d)). In addition, the boundaries of the distal wall are much smoother in the pulse-inversion harmonic ARFI image compared with the other ARFI images.

The bright, coherent clutter signal observed in the B-mode image presents as a region of increased displacement greater than 3 μm within the jugular vein near the proximal wall of the carotid artery, indicated by the yellow arrows, in the matched 4-MHz fundamental ARFI image (FIG. 5(a)). Similar to the trend observed in the B-mode amplitude, this region of increased displacement is also observed in the 8-MHz fundamental ARFI image (FIG. 5(b)), but is reduced in the filtered harmonic ARFI image (FIG. 5(c)), and is least obvious in the pulse-inversion harmonic ARFI image (FIG. 5(d)).

Measurements of the mean displacement and mean normalized cross-correlation values ±1 standard deviation within the proximal wall, distal wall, and lumen of the carotid artery portrayed in FIGS. 5(a)-5(d) are listed in Table I for each ARFI image. The locations of the measurement regions, which were based upon the pulse-inversion harmonic ARFI image, are indicated by the white-dashed contours in FIG. 5(a). Estimates of the ARFI-induced tissue displacements are of reduced magnitude and have less variance in the distal wall in the harmonic ARFI images (Table I). This is especially true for the pulse-inversion harmonic ARFI image, which also has the lowest displacement variance in the proximal wall. In the lumen, the magnitude and standard deviation of the axial displacement is significantly greater in the harmonic ARFI images and is greatest in the pulse-inversion harmonic ARFI image. The normalized cross-correlation values are quite similar within the proximal and distal walls for all tracking methods. In the lumen, however, the normalized cross-correlation values in the harmonic ARFI images are significantly reduced in magnitude and have greater variance, especially in the pulse-inversion harmonic ARFI image.

Figure 4:
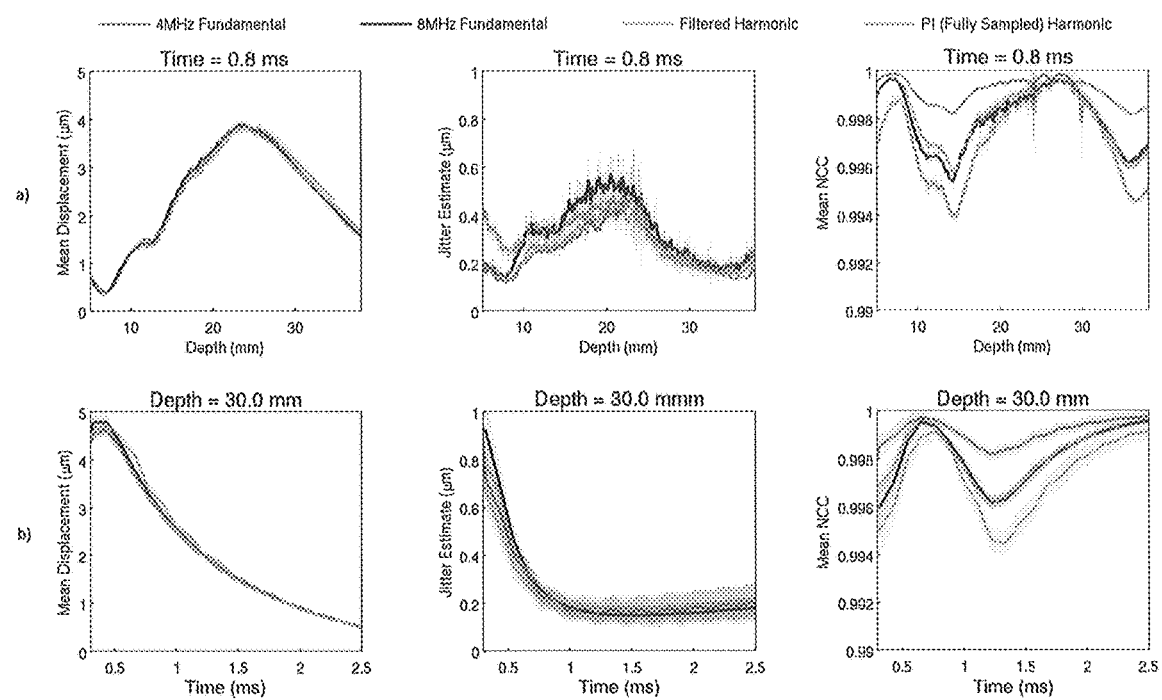
FIGS. 4a-4b are graphs illustrating the mean axial displacement, jitter estimate, and mean normalized cross-correlation (NCC) profiles among the fundamental and harmonic tracking methods acquired in an E=9 kPa homogeneous, elastic, tissue-mimicking ultrasound phantom with a focal depth of 30 mm according to some embodiments.
Figure 5:
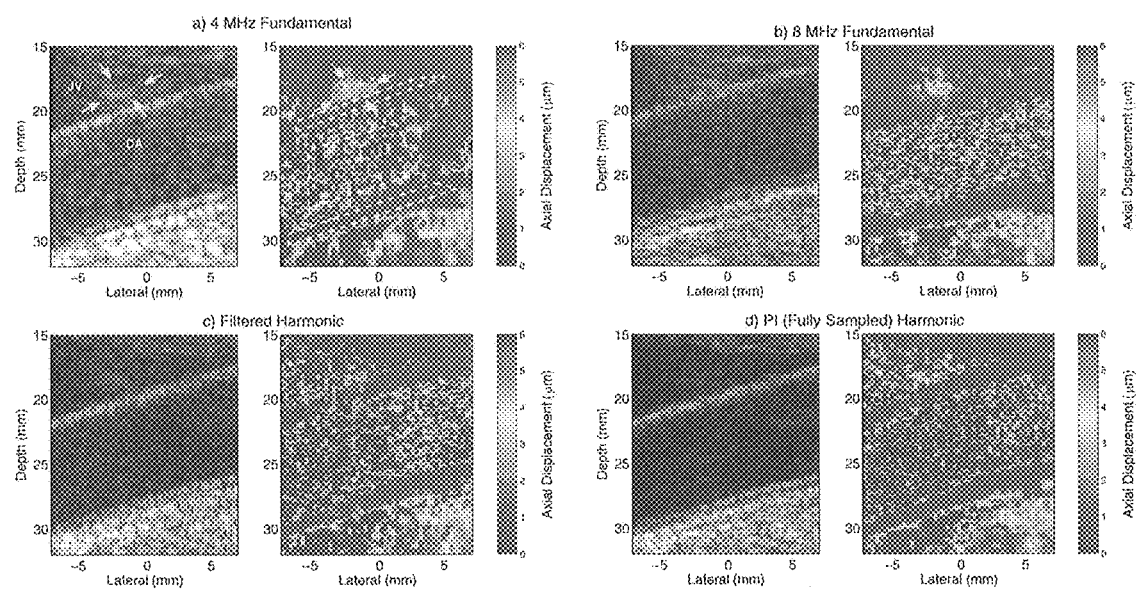
FIGS. 5a-5d are B-mode and ARFI ultrasound images illustrating a 4-MHz fundamental signal (FIG. 5a), an 8-MHz fundamental signal (FIG. 5b), a filtered harmonic signal (FIG. 5c) and a fully sampled pulse-inversion (PI) harmonic signal (FIG. 5d) according to some embodiments.

TABLE I axial displacement estimates and normalized cross-correlation values for ARFI Images in FIG. 4.

|  | Proximal wall | Distal wall | Lumen |
|---|---|---|---|
| Axial displacement (μm) | | | |
| 4-MHz fundamental | 0.83 ± 0.45 | 0.81 ± 0.47 | 3.14 ± 3.15 |
| 8-MHz fundamental | 0.69 ± 0.48 | 0.92 ± 1.02 | 3.73 ± 3.65 |
| Filtered harmonic | 0.93 ± 1.07 | 0.73 ± 0.38 | 7.06 ± 6.44 |
| PI (Fully sampled) harmonic | 0.73 ± 0.41 | 0.58 ± 0.28 | 13.66 ± 10.68 |
| Normalized cross-correlation | | | |
| 4-MHz fundamental | 0.997 ± 0.005 | 0.999 ± 0.002 | 0.973 ± 0.041 |
| 8-MHz fundamental | 0.994 ± 0.008 | 0.996 ± 0.006 | 0.944 ± 0.076 |
| Filtered harmonic | 0.991 ± 0.013 | 0.997 ± 0.003 | 0.863 ± 0.143 |
| PI (Fully sampled) harmonic | 0.991 ± 0.014 | 0.994 ± 0.014 | 0.738 ± 0.207 |

Figure 6:
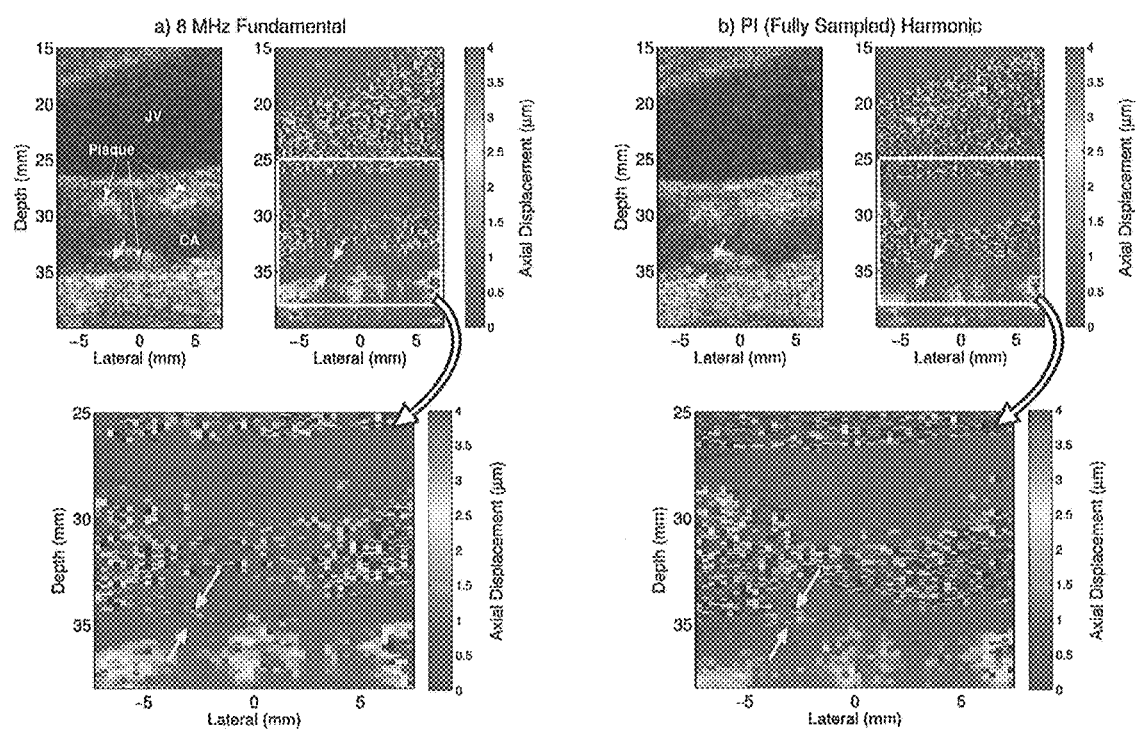
FIGS. 6a-6b are in vivo B-mode and ARFI ultrasound images for an 8-MHz fundamental signal (FIG. 6a) and a fully sampled pulse-inversion harmonic signal (FIG. 6b) of a carotid artery (CA) and jugular vein (JV) in a subject with known carotid artery plaques according to some embodiments.

FIGS. 6a-6b show matched B-mode and ARFI images of a carotid artery and jugular vein in a subject with known carotid artery plaques. For conciseness, only the 8-MHz fundamental and pulse-inversion harmonic images are portrayed. In the B-mode images, the plaque boundaries are better visualized in the pulse-inversion harmonic image (FIG. 6(b)) compared with the fundamental image (FIG. 6(a)). Despite similar contrast values of 18.93 and 19.04 db, this qualitative comparison is consistent with the improved CNR value of 1.20 compared with 0.93 for the pulse-inversion harmonic and 8-MHz fundamental B-mode images, respectively.

In the pulse-inversion harmonic ARFI image (FIG. 6(b)) there is improved delineation of the blood-vessel interface at the proximal and distal walls of the jugular vein compared with the 8-MHz fundamental ARFI image (FIG. 6(a)). Within the carotid artery, the magnitude of displacements in the narrow region of the lumen is similar in magnitude to the displacements in the adjacent plaque and arterial wall regions in the 8-MHz fundamental ARFI image (FIG. 6(a)), making it difficult to visualize the lumen and identify plaque boundaries. The greater displacements observed within the lumen of the carotid artery in the pulse-inversion harmonic ARFI image (FIG. 6(b)) improve the discrimination of blood from soft tissues and make it easier to visualize the plaque boundaries.

Improved feature detection within the plaques is achieved with the pulse-inversion harmonic tracking method. To illustrate this, an expanded view of the region of interest indicated by the solid white lines has been provided for the ARFI images in FIGS. 6(a) and 6(b). In these expanded views, a region of increased displacement that is approximately 2 μm within the distal wall carotid plaque, indicated by yellow arrows, can be seen in the pulse-inversion harmonic ARFI image (FIG. 6(b)). This particular feature is not readily identified in the 8-MHz fundamental ARFI image (FIG. 6(a)), but is spatially registered with a hypoechoic region of similar geometry that can be seen in both the fundamental and pulse-inversion harmonic B-mode images.

Figure 7:
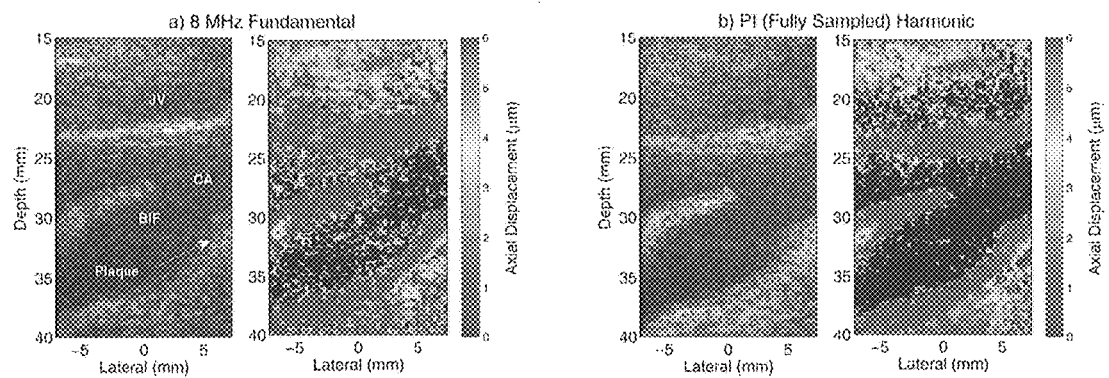
FIGS. 7a-7b are in vivo B-mode and ARFI images of an 8-MHz fundamental signal (FIG. 7a) and a fully sampled pulse inversion (PI) harmonic signal (FIG. 7b) image according to some embodiments.

FIGS. 7(a)-7(b) show matched B-mode and ARFI, 8-MHz fundamental and pulse-inversion harmonic images acquired at the bifurcation of a carotid artery in a subject with a small amount of plaque on the distal wall. Regions of low correlation in the ARFI images have been masked by setting displacement values with a normalized cross-correlation value less than 0.97 to black.

Within the lumen of the carotid artery in the pulse inversion harmonic B-mode image (FIG. 7(b)), there is suppressed clutter compared with the 8-MHz fundamental B-mode image (FIG. 7(a)). The pulse-inversion harmonic method demonstrates significant improvements in contrast and CNR; 20.84 db contrast and 1.35 CNR for the pulse-inversion harmonic B-mode image compared with 16.31 db contrast and 0.77 CNR for the 8-MHz fundamental B-mode image.

The reduced normalized cross-correlation values associated with displacement estimates in regions of blood demonstrated by the pulse-inversion harmonic ARFI images (Table I) allow for improved discrimination of blood from regions of soft tissue. With the correlation threshold in FIGS. 7(a)-7(b), the blood-vessel interfaces along the proximal and distal walls of the carotid artery are more clearly delineated in the pulse-inversion harmonic ARFI image (FIG. 7(b)) compared with the 8-MHz fundamental ARFI image (FIG. 7(a)). In addition, the correlation threshold removed displacement noise from the jugular vein in the pulse-inversion harmonic ARFI image (FIG. 7(b)) that cannot be identified in the 8-MHz fundamental ARFI image (FIG. 7(a)).

Figures 8A, 8B, 8C:
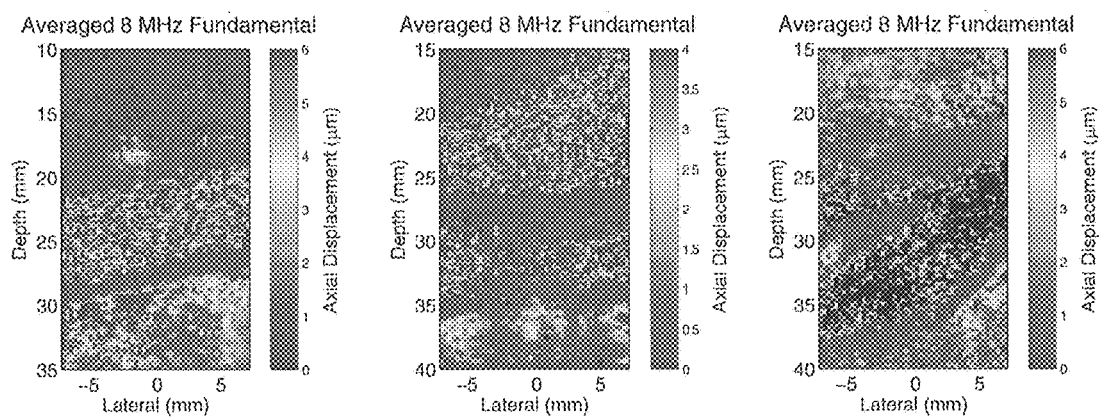
FIGS. 8a-8c are in vivo ARFI images of an averaged 8-MHz fundamental signal according to some embodiments.

FIGS. 8(a)-8(c) show ARFI images for the averaged 8-MHz fundamental data collected in the subjects shown previously in FIGS. 5-7 as previously described, this averaged data was created by summing the identical polarity 8-MHz fundamental radio-frequency data according to the fully sampled pulse-inversion harmonic approach (FIG. 2(b)) described herein. In comparing the non-averaged and averaged 8-MHz fundamental ARFI images (i.e., comparing FIG. 5(b) with FIG. 8(a), FIG. 6(a) with FIG. 8(b), and FIG. 7(a) with FIG. 8(c)), no noticeable difference is observed.

Accordingly, a pulse-inversion harmonic method with an improved temporal sampling frequency to monitor the transient deformation from an impulsive acoustic radiation force excitation is demonstrated. In phantoms and in vivo experiments, the pulse-inversion harmonic tracking method is compared with a filtered harmonic approach and conventional techniques that use the fundamental component of returned echoes to form a displacement estimate. In the phantom experiments (FIGS. 4(a)-4(b)) the jitter increased and normalized cross-correlation decreased with increasing displacement magnitude, which is consistent with ARFI imaging simulations and experiments reported by others. M. L. Palmeri, S. A. Mcaleavey, G. E. Trahey, and K. R. Nightingale, "Ultrasonic tracking of acoustic radiation force-induced displacements in homogeneous media," IEEE Trans. Ultrason. Ferroelectr. Freq. Control, vol. 53, no. 7, pp. 1300-1313, July. 2006' S. A. Mcaleavey, K. R. Nightingale, and G. E. Trahey, "Estimates of echo correlation and measurement bias in acoustic radiation force impulse imaging," IEEE Trans. Ultrason. Ferroelectr. Freq. Control, vol. 50, no. 6, pp. 631-641, 2003. Subtle differences in the pulse-inverted transmit signals, resulting from nonlinearities in the ultrasound system, may be responsible for the slight oscillation observed through time (FIG. 4(b)) in the 4-MHz fundamental, filtered harmonic, and pulse-inversion harmonic data sets created from the pulse-inverted echoes. Despite this small artifact, the relatively smooth profiles observed through time (FIG. 4(b)) demonstrate how the fully sampled pulse-inversion harmonic method (FIG. 2(b)) can be used to reliably track the transient deformation response without a degraded temporal sampling frequency. The slight decrease in normalized cross-correlation values observed with the pulse-inversion harmonic method (FIGS. 4(a)-4(b)) is likely due to motion that occurs between pulse-inverted transmits. The small magnitude of this decorrelation seems reasonable given the relatively small displacements and does not appear to increase jitter. For the various focal depths and phantom stiffnesses investigated in this study, any difference in the harmonic and fundamental tracking methods appears to be independent of shear wave speeds and focal effects.

No visible clutter was observed in the homogeneous phantoms used in this study, such that no improvement resulting from clutter suppression associated with the harmonic methods was expected in the phantom experiments. This can explain the similarity between the 8-MHz fundamental method with the 8-MHz filtered and pulse-inversion harmonic methods. In addition, the similarity of the higher frequency tracking methods (filtered harmonic, pulse-inversion harmonic, and 8-MHz fundamental) compared with the lower frequency 4-MHz fundamental tracking method in phantoms suggests that improvements, if any, resulting from an increased frequency are also insignificant. Similar results were observed in simulations by Palmeri et al. (M. L. Palmeri, S. A. Mcaleavey, G. E. Trahey, and K. R. Nightingale, "Ultrasonic tracking of acoustic radiation force-induced displacements in homogeneous media," IEEE Trans. Ultrason. Ferroelectr. Freq. Control, vol. 53, no. 7, pp. 1300-1313, July 2006), who demonstrated that an increased tracking frequency can reduce bias and jitter only if the transducers' fractional bandwidth, centered about the tracking frequency, is held constant with increasing tracking frequency. This would require the absolute bandwidth to scale proportionately with the increasing frequency. The fixed bandwidth about the center frequency of the transducer likely explains why the theoretical improvements predicted by the Cramér-Rao lower bound (S. Bjaerum, H. Torp, and K. Kristoffersen, "Clutter filters adapted to tissue motion in ultrasound color flow imaging," IEEE Trans, Ultrason. Ferroelectr. Freq. Control, vol. 49, no. 6, pp. 693-704, June 2002) were not observed. Without clutter and with no improvements resulting from increased tracking frequency, the similarity between the harmonic and fundamental track-ing methods observed in the phantoms is not surprising. Despite the lack of improvement shown in the homogeneous phantoms, these results indicate that any improvement observed with harmonic tracking methods in a more challenging environment, such as in vivo imaging, cannot be attributed to increased tracking frequency and is likely due to suppressed clutter.

The use of harmonic tracking methods appears to significantly improve the quality of in vivo ARFI imaging. In general, an improved sensitivity to discriminate blood from soft tissues, making it easier to detect the blood-vessel interface, and improved visualization of arterial features was demonstrated in the harmonic ARFI images compared with the fundamental ARFI images in FIGS. 5-7. The comparison between averaged 8-MHz fundamental ARFI images (FIG. 8) with the non-averaged 8-MHz fundamental ARFI images (FIGS. 5(b), 6(a), and 7(a)), suggests that the low-pass filter effect from the summation of pulses temporally separated is negligible. These results also suggest that the improvements observed in the pulse-inversion harmonic images are not attributed to a simple averaging effect. The reduced clutter observed in the harmonic B-mode images, supported by improved contrast and CNR, suggests that the improvements observed in the harmonic ARFI images in vivo are also due to a reduction in clutter.

Clutter suppression achieved with harmonic tracking methods is also supported by differences in the measured displacements and associated normalized cross-correlation values between the fundamental and harmonic ARFI images (Table I). It has been well described in Doppler literature that clutter from stationary or slowly moving tissues can result in an underestimation of the measured blood velocities (S. Bjaerum, H. Torp, and K. Kristoffersen, "Clutter filters adapted to tissue motion in ultrasound color flow imaging," IEEE Trans. Ultrason, Ferroelectr. Freq. Control, vol. 49, no. 6, pp. 693-704, June 2002). Removal of clutter signals would therefore reduce this bias and lead to an increase in the measured displacements of the blood. In addition, because stationary clutter is significantly more correlated and of higher intensity than echoes from flowing blood, the removal of clutter signals would lead to decreased normalized cross-correlation values and subsequently, according to Bjaerum et al., increased displacement variance within the lumen. The increased displacement magnitude, decreased normalized cross-correlation, and increased displacement variance demonstrated in the lumen of FIGS. 5(a)-5(d) (Table I) with the harmonic ARFI images, especially the pulse-inversion harmonic ARFI image (FIG. 5(d)), are therefore all indicative of reduced bias associated with the removal of stationary or slowly moving clutter. Similar arguments can also explain the increased displacement in FIG. 6(b) and the decreased normalized cross-correlation in FIG. 7(b) within the lumen for the pulse-inversion harmonic ARFI images.

The decreased B-mode amplitude and decreased ARFI displacement observed in the harmonic images near the proximal wall in the jugular vein in FIGS. 5(a)-5(d) may be due to a suppression of clutter. Although the specific source is unknown, this region presents as a large, bright echo, representative of ring-down reverberation in the 4-MHz fundamental B-mode image. In the spatially-matched ARFI image, this artifact presents as a region of increased displacement that may be biased by clutter from overlying tissues. The near-removal of this clutter signal in the harmonic images, especially in the pulse-inversion harmonic images, suggests that harmonic tracking methods may be less susceptible to such artifacts. Reduced bias via suppression of diffuse clutter may also account for the improved visualization of the small region of increased displacement within the distal wall plaque in the pulse-inversion harmonic ARFI image in FIG. 6(b). With the hypoechoic region of similar spatial location and geometry observed in both the fundamental and harmonic B-mode images of FIGS. 6(a)-6(b), this region may be a structural feature of the plaque and not an imaging artifact. Improved visualization of such small features may be promising for ARFI imaging methods aimed at differentiating carotid plaques containing small, soft lipid pools believed to be more vulnerable from more stable, calcified plaques. In addition to reduced bias, the decreased variance in displacements measured within the stiff arterial walls of the harmonic ARFI images in FIGS. 5(a)-5(d) (Table I) measured in the pulse-inversion harmonic ARFI image suggests harmonic tracking may also reduce jitter in displacement estimates.

The improvements demonstrated in vivo appear consistent with a removal of clutter. Without wishing to be bound by any particular theory, it is noted that the specific mechanisms of the observed improvements may be somewhat unclear. Unfortunately, clutter-generating phantoms do not currently exist commercially and reliably generating clutter in a controlled experiment remains a challenge. In addition, although recent methods allow for simulating the nonlinear propagation of waves and can account for multiple reflections and scattering, these methods do not allow for investigating small micrometer-size ARFI displacements. For these reasons, the in vivo demonstration of harmonic tracking is provided. Nonetheless, because the 4-MHz fundamental, filtered harmonic, and pulse-inversion harmonic images were created from the same radio-frequency data, with the 8-MHz fundamental acquisition occurring 210 ms later in time (FIG. 3), it seems unlikely that any in vivo motion could account for the demonstrated improvements. In addition, the improvements in harmonic image quality in vivo were consistent across multiple acquisitions and scanning locations separated in time, such that the images were temporally and spatially stable.

Although embodiments of the invention are described with respect to in vivo pulse-inversion harmonic images in blood vessels such as the carotid artery and jugular vein, any suitable region of interest may be imaged or interrogated using the techniques described herein. For example, other ARFI applications, including cardiac and abdominal imaging, in which large amounts of clutter from near-field reverberation are known to degrade B-mode image quality, may also benefit from the reduced bias and jitter of harmonic tracking methods. The potentially improved estimation of soft tissue displacements may also provide more accurate estimates of wave velocity for acoustic radiation force shear-wave-based methods that track the off-axis deformation response to quantify material properties. Examples of shear-wave techniques are described in U.S. Pat. No. 6,764,448 to Trahey and U.S. Pat. No. 8,118,744 Palmeri, the disclosures of which are hereby incorporated by reference in their entities. That is, the off-axis deformation response of a shear wave that propagates in a direction orthogonal to the axis of excitation may be tracked using the pulse-inversion harmonic ultrasound sequences described herein. Although the pulse-inversion harmonic methods are described herein with respect to relatively small displacements associated with acoustic radiation force-based elasticity imaging methods, it should be understood that pulse-inversion harmonic analysis may also be used in other ultrasound-based elasticity imaging methods such as strain imaging and shear wave imaging.

The foregoing is illustrative of the present invention and is not to be construed as limiting thereof. Although a few example embodiments of this invention have been described, those skilled in the art will readily appreciate that many modifications are possible in the example embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications, to the disclosed embodiments, as well as other embodiments, are intended to be included within the scope of the appended claims. The invention is defined by the following claims, with equivalents of the claims to be included therein.

That which is claimed is:

1. An ultrasound system for estimating tissue deformation in ultrasound elasticity imaging, the system comprising:
   an ultrasound transducer configured to receive ultrasound echo signals from tissue in a region of interest at a plurality of ultrasound transducer channels;
   a beamformer configured to receive ultrasound channel signals from the plurality of ultrasound transducer channels and to focus and sum the ultrasound channel signals to form a focused radiofrequency (RF) signal; and
   a harmonic data processor configured to receive the RF signal, to extract a plurality of harmonic data sets comprising harmonic components from the RF signal, the plurality of harmonic data sets comprising combined echo signals from pairs of pulse inverted signals, the pairs of pulse inverted signals comprising:
      at least a first pair of pulse inverted signals; and
      at least a second pair of pulse inverted signals, the second pair of pulse inverted signals comprising one of the pulse inverted signals of the first pair of pulse inverted signals, and
   to estimate tissue deformation in the region of interest using the plurality of harmonic data sets.

2. The ultrasound system of claim 1, wherein the ultrasound transducer is configured to transmit phase inverted waveforms alternatively in a single tracking location and to receive corresponding echo signals at the transducer, and the harmonic data processor is configured to sum phase inverted signals such that the phase inverted signals cancel a fundamental signal and odd harmonic signals while doubling even harmonics to provide the harmonic data sets.

3. The ultrasound system of claim 2, wherein the harmonic data processor is configured to estimate the tissue deformation by at least one of calculating a maximum displacement occurring through time, a displacement at a given time, a time to percent recovery of a maximum displacement, tissue velocities, blood velocities, and cross-correlation values.

4. The ultrasound system of claim 1, wherein the ultrasound transducer is configured to create a tissue displacement using acoustic radiation force.

5. An ultrasound method for estimating tissue deformation in ultrasound elasticity imaging, the method comprising:
   receiving ultrasound echo signals from tissue for a region of interest from an ultrasound transducer at a plurality of ultrasound transducer channels;
   focusing and summing the ultrasound channel signals to form a focused radiofrequency signal at a beamformer;

extracting a plurality of harmonic data sets comprising harmonic components from the RF signal with a harmonic data processor, the plurality of harmonic data sets comprising combined echo signals from pairs of pulse inverted signals, the pairs of pulse inverted signals comprising:
- at least a first pair of pulse inverted signals; and
- at least a second pair of pulse inverted signals, the second pair of pulse inverted signals comprising one of the pulse inverted signals of the first pair of pulse inverted signals; and estimating tissue deformation in the region of interest using the plurality of harmonic data sets.

6. The method of claim 5, further comprising:
transmitting phase inverted waveforms alternatively in a single tracking location by the ultrasound transducer;
receiving corresponding echo signals at the transducer; and
summing phase inverted signals at the harmonic data processor such that the phase inverted signals cancel a fundamental signal and odd harmonic signals while doubling even harmonics to provide the harmonic data sets.

7. The method of claim 6, wherein estimating the tissue deformation comprises at least one of calculating a maximum displacement occurring through time, calculating a displacement at a given time, calculating a time to percent recovery of a maximum displacement, calculating tissue velocities, calculating blood velocities, and calculating cross-correlation values.

8. The method of claim 5, further comprising creating a tissue displacement using acoustic radiation force from the ultrasound transducer.

* * * * *